United States Patent
Uemura et al.

(10) Patent No.: US 10,434,029 B2
(45) Date of Patent: Oct. 8, 2019

(54) METHOD FOR DETERMINING LEG-PHASE SHIFT TIMING, LEG-PHASE SHIFT TIMING DETERMINATION APPARATUS, METHOD FOR CONTROLLING WALKING ASSISTANCE, AND WALKING ASSISTANCE APPARATUS

(71) Applicant: Osaka University, Osaka (JP)

(72) Inventors: Mitsunori Uemura, Osaka (JP); Fumio Miyazaki, Osaka (JP); Hiroaki Hirai, Osaka (JP)

(73) Assignee: Osaka University (JP)

( * ) Notice: Subject to any disclaimer, the term of this patent is extended or adjusted under 35 U.S.C. 154(b) by 186 days.

(21) Appl. No.: 15/324,136

(22) PCT Filed: Jun. 23, 2015

(86) PCT No.: PCT/JP2015/067956
§ 371 (c)(1),
(2) Date: Jan. 5, 2017

(87) PCT Pub. No.: WO2016/006432
PCT Pub. Date: Jan. 14, 2016

(65) Prior Publication Data
US 2018/0177667 A1   Jun. 28, 2018

(30) Foreign Application Priority Data
Jul. 10, 2014 (JP) .................. 2014-141865

(51) Int. Cl.
A61H 3/00 (2006.01)
A61F 5/01 (2006.01)
(Continued)

(52) U.S. Cl.
CPC ............... *A61H 3/00* (2013.01); *A61B 5/112* (2013.01); *A61H 1/024* (2013.01); *B25J 9/0006* (2013.01);
(Continued)

(58) Field of Classification Search
None
See application file for complete search history.

(56) References Cited

U.S. PATENT DOCUMENTS

2013/0150980 A1* 6/2013 Swift .................. A61F 2/68
623/24

FOREIGN PATENT DOCUMENTS

JP    2003-116893    4/2003
JP    2008-175559    7/2008
(Continued)

OTHER PUBLICATIONS

"Development of a Knee Assist Device with a Variable Stiffness Mechanism" Ippei Kamada, Mitunori Uemura, Hiroaki Hirai, Fumio Miyazaki, 1A1-V07(1)to 1A1-V07(3), No. 12-3 Proceedings of the 2012 JSME Conference on Robotics and Mechatronics, Hamamatsu, Japan, May 27-29, 2012.
(Continued)

*Primary Examiner* — David H Willse
(74) *Attorney, Agent, or Firm* — Jordan and Koda, PLLC

(57) ABSTRACT

A walking assistance apparatus includes: a walking assistance attachment to be attached to a leg of a human body and including a variable stiffness mechanism having stiffness that is changeable in a direction where the human bends and stretches the knee by motor driving; and a controller. The controller includes a foot-end motion calculation part configured to receive an output from a sensor to detect motion of a leg and successively calculate a relative velocity of a foot end with reference to a waist of the human body; and
(Continued)

a leg state determination part configured to determine shift timing between a swing phase and a stance phase based on the relative velocity of the foot end.

19 Claims, 9 Drawing Sheets

(51) Int. Cl.
| | |
|---|---|
| *A61F 2/64* | (2006.01) |
| *A61F 2/70* | (2006.01) |
| *A61B 5/11* | (2006.01) |
| *B25J 9/00* | (2006.01) |
| *B25J 9/10* | (2006.01) |
| *A61H 1/02* | (2006.01) |
| *A61F 2/76* | (2006.01) |
| *A61F 2/50* | (2006.01) |
| *A61B 5/05* | (2006.01) |

(52) U.S. Cl.
CPC ............... *B25J 9/104* (2013.01); *A61B 5/05* (2013.01); *A61B 5/1121* (2013.01); *A61B 5/1123* (2013.01); *A61B 2562/0219* (2013.01); *A61B 2562/0247* (2013.01); *A61F 2002/503* (2013.01); *A61F 2002/5073* (2013.01); *A61F 2002/704* (2013.01); *A61F 2002/763* (2013.01); *A61F 2002/7625* (2013.01); *A61H 2003/001* (2013.01); *A61H 2201/0192* (2013.01); *A61H 2201/1207* (2013.01); *A61H 2201/164* (2013.01); *A61H 2201/165* (2013.01); *A61H 2201/1671* (2013.01); *A61H 2201/5007* (2013.01); *A61H 2201/5058* (2013.01); *A61H 2201/5069* (2013.01); *A61H 2201/5071* (2013.01); *A61H 2201/5079* (2013.01); *A61H 2201/5084* (2013.01); *A61H 2203/0406* (2013.01); *A61H 2205/10* (2013.01)

(56) References Cited

FOREIGN PATENT DOCUMENTS

| | | | |
|---|---|---|---|
| JP | 2010-148637 | 7/2010 | |
| JP | 2010-148637 A * | 7/2010 | ............. A61H 1/024 |
| JP | 2010-148759 | 7/2010 | |
| JP | 2010-273748 | 12/2010 | |
| JP | 2011-206289 | 10/2011 | |
| JP | 2011-239887 | 12/2011 | |
| JP | 2012-50718 | 3/2012 | |
| JP | 2014-50490 | 3/2014 | |
| JP | 2014-184047 | 10/2014 | |
| WO | WO-2010/074160 | 7/2010 | |

OTHER PUBLICATIONS

"A New Mechanism of Stiffness Adjustment for Lightweight and Small Devices" Mitsunori Uemura and Sadao Kawamura (Ritsumeikan Univ.), No. 10-4 Proceedings of the 2010 JSME Conference on Robotics and Mechatronics, Asahikawa, Japan, Jun. 13-16, 2010.

* cited by examiner

SWING PHASE

STANCE PHASE

METHOD FOR DETERMINING LEG-PHASE SHIFT TIMING, LEG-PHASE SHIFT TIMING DETERMINATION APPARATUS, METHOD FOR CONTROLLING WALKING ASSISTANCE, AND WALKING ASSISTANCE APPARATUS

BACKGROUND OF THE INVENTION

The present invention relates to techniques of determining the walking state of a user and assisting the walking motion of the user.

Recently various walking assistance apparatuses have been proposed, which are of a lower-limb mounted type and are configured to assist the walking of persons who cannot perform walking motions well or have difficulty in walking for a long time because of their weakened or declined muscle strength in the lower limbs. Apparatuses of this type include a motor to give a torque to a knee joint or the like, and a detector configured to detect the walking state of a walker for suitable controlling to give the torque. The walking state of a walker is determined using a swing phase and a stance phase of the legs during walking or walking upstairs/downstairs. Therefore the detector typically includes a pressure sensor of a sole-attached type or a gravity sensor of a waist-mounted type, by which the timing when the legs come into contact with the ground (hereinafter called grounding timing) can be detected, and these phases of the legs are determined based on the grounding timing (see Patent Literatures 1 to 7, for example). A walking analysis apparatus also is proposed, which is configured to calculate the time when the leg is left from the ground and the time when the leg is grounded of a walker who is wearing an acceleration sensor and an angular velocity sensor on the leg. The analysis apparatus is configured to perform the calculations based on the absolute values of the acceleration that are detected, and set the timing of a maximum value in the first half of the detected data for each step as the time of leaving from the ground and set the timing of a maximum value in the latter half thereof as the grounding time (Patent Literature 8).

Non-Patent Literature 1 proposes a variable stiffness mechanism that is small and light-weight. The variable stiffness mechanism includes two frames coupled via a rotating member, a ball screw mechanism, a linear spring, and a motor. The linear spring is expandable between the two frames, and the elasticity of the linear spring can be changed using the ball screw mechanism, so that the linear spring has maximum elasticity energy when the stiffness of the mechanism is the maximum.

CITATION LIST

Patent Literatures

Patent Literature 1 Japanese Patent Application Laid-Open No. 2011-239887
Patent Literature 2 WO2010/074160
Patent Literature 3 Japanese Patent Application Laid-Open No. 2003-116893
Patent Literature 4 Japanese Patent Application Laid-Open No. 2010-148759
Patent Literature 5 Japanese Patent Application Laid-Open No. 2010-273748
Patent Literature 6 Japanese Patent Application Laid-Open No. 2011-206289
Patent Literature 7 Japanese Patent Application Laid-Open No. 2010-148637
Patent Literature 8 Japanese Patent Application Laid-Open No. 2008-175559

Non Patent Literature

Non-Patent Literature 1 "Development of a Knee Assist Device with a Variable Stiffness Mechanism" Ippei KAMADA, Mitunori UEMURA, Hiroaki HIRAI, Fumio MIYAZAKI, 1A1-V07(1) to 1A1-V07(3), No. 12-3 Proceedings of the 2012 JSME Conference on Robotics and Mechatronics, Hamamatsu, Japan, May 27-29, 2012

SUMMARY OF THE INVENTION

When a pressure sensor of a sole-attached type is used in the apparatus, such a sensor receives impact when contact is made with the ground. Therefore the apparatus may deteriorate in accuracy or break with use. It may be difficult to attach a sensor on the sole in some types of walking assistance attachment. To assist both legs as a whole, some attachments include an angle sensor to measure the angle of joints so as to detect and predict the walking state. Attachments of this type require obtaining angles of all joints of both legs of a person by the angle sensor, and therefore such an attachment is complicated in structure and increases in size, weight, and cost. Such an attachment also has a certain limit in the operability because it requires troublesome operations in wearing and removing. If the assist is aimed only for the knees, an attachment for this aim has limitations because a pressure sensor cannot be attached to the sole, and has to be attached only to a thigh and a lower thigh on one leg. Therefore, for such an attachment, no effective method for detecting and predicting walking states has been developed. Since a sensor to detect the grounding is to detect the grounding time only, it is difficult to know the details of the walking state from such information on grounding. Therefore it is impossible in principle to predict the walking state in the future from such information.

Patent Literature 1 and Patent Literature 2 describe algorithm to determine the switching timing between swing legs/stance legs based on the horizontal foot speed. This horizontal foot speed, however, is a foot speed of the swing leg viewed from the stance leg, and therefore it requires determination as to whether which leg is the stance leg using a pressure sensor on the sole. In order to find the horizontal foot speed, the angles and the angular velocities of all joints of both legs also are required. Therefore, the determination algorithm of Patent Literature 1 and Patent Literature 2 requires a pressure sensor on the sole and attitude sensors for both legs.

In Patent Literature 8, walking analysis is made using the absolute values of the acceleration detected by the acceleration sensor attached to the foot. When the absolute values of acceleration are used as in this literature, it is difficult to analyze various types of walking modes other than a normal walking mode on the level land. The configuration of this literature is not applicable to a walking assistance attachment in real time. Non-Patent Literature 1 relates to a variable stiffness mechanism, which is not configured to control to change the stiffness of the variable stiffness mechanism in association with a walking state.

In view of them, the present invention aims to provide a leg-phase shift timing determination apparatus capable of more precisely determining the shift timing between a swing phase and a stance phase of the legs using a relative foot-end velocity with reference to a reference position of the human body without a need of a pressure sensor on the sole, and such a method.

The present invention aims to provide a walking assistance apparatus capable of assisting the knee joints favorably in accordance with the walking state and a method for controlling the apparatus.

A leg-phase shift timing determination apparatus according to the present invention includes: a walking information acquisition unit configured to receive an output from a sensor to detect motion of a leg of a human body and successively calculate a relative velocity of a foot end with reference to a reference part of the human body; and a leg state determination unit configured to determine shift timing between a swing phase and a stance phase based on the relative velocity of the foot end.

According to the present invention, the walking information acquisition unit receives an output from a sensor and successively calculates a relative velocity of a foot end with reference to a reference part of the human body, e.g., a waist. Then the leg state determination unit determines shift timing between a swing phase and a stance phase based on the relative velocity of the foot end calculated by the walking information acquisition unit. The shift timing is determined whether it shifts from a swing phase to a stance phase or from a stance phase to a swing phase. Therefore, shift timing between a swing phase and a stance phase can be determined more precisely based on the relative foot-end velocity with reference to the reference part of the human body.

A method for determining leg-phase shift timing according to the present invention includes: a walking information acquisition step of receiving an output from a sensor to detect motion of a leg of a human body and successively calculating a relative velocity of a foot end with reference to a reference part of the human body; and a leg state determination step of determining shift timing between a swing phase and a stance phase based on the relative velocity of the foot end calculated at the walking information acquisition step.

A walking assistance apparatus according to the present invention includes: a walking assistance attachment to be attached to a leg of a human body and including a variable stiffness mechanism having stiffness that is changeable in a direction where the human bends and stretches the knee; the leg-phase shift timing determination apparatus as stated above; and a stiffness control unit configured to increase the stiffness of the variable stiffness mechanism at shift timing from the swing phase to the stance phase and to decrease the stiffness of the variable stiffness mechanism at shift timing from the stance phase to the swing phase.

A method for controlling walking assistance according to the present invention is for a walking assistance attachment to be attached to a leg of a human body and including a variable stiffness mechanism having stiffness that is changeable in a direction where the human bends and stretches the knee. The method includes: a walking information acquisition step of receiving an output from a sensor to detect motion of the leg and successively calculating a relative velocity of a foot end with reference to a reference part of the human body; a leg state determination step of determining shift timing between a swing phase and a stance phase based on the relative velocity of the foot end calculated at the walking information acquisition step; and a stiffness control step of increasing the stiffness of the variable stiffness mechanism at shift timing from the swing phase to the stance phase and decreasing the stiffness of the variable stiffness mechanism at shift timing from the stance phase to the swing phase.

According to the present invention, the walking assistance attachment is attached to a leg of a human body and the variable stiffness mechanism changes the stiffness to adjust the torque to be given in the direction where the human bends and stretches the knee. For instance, the shift timing between a swing phase and a stance phase of the walking assistance attachment is determined by the leg-phase shift timing determination apparatus having a sensor to detect a motion of the leg. The stiffness control unit increases the stiffness of the variable stiffness mechanism at shift timing from the swing phase to the stance phase and decreases the stiffness of the variable stiffness mechanism at shift timing from the stance phase to the swing phase. In this way, walking states can be determined to find shift timing between a swing phase and a stance phase, and the stiffness can be increased or decreased in accordance with the determination. Thereby the knees can be assisted favorably.

According to the present invention, shift timing between a swing phase and a stance phase can be determined more precisely based on relative foot-end velocity with reference to a reference part of the human body without the need of a sensor on the sole.

According to the present invention, the stiffness can be increased or decreased favorably to assist knees in accordance with shift timing between a swing phase and a stance phase of the legs.

DESCRIPTION OF THE PREFERRED EMBODIMENTS

Figure 1:
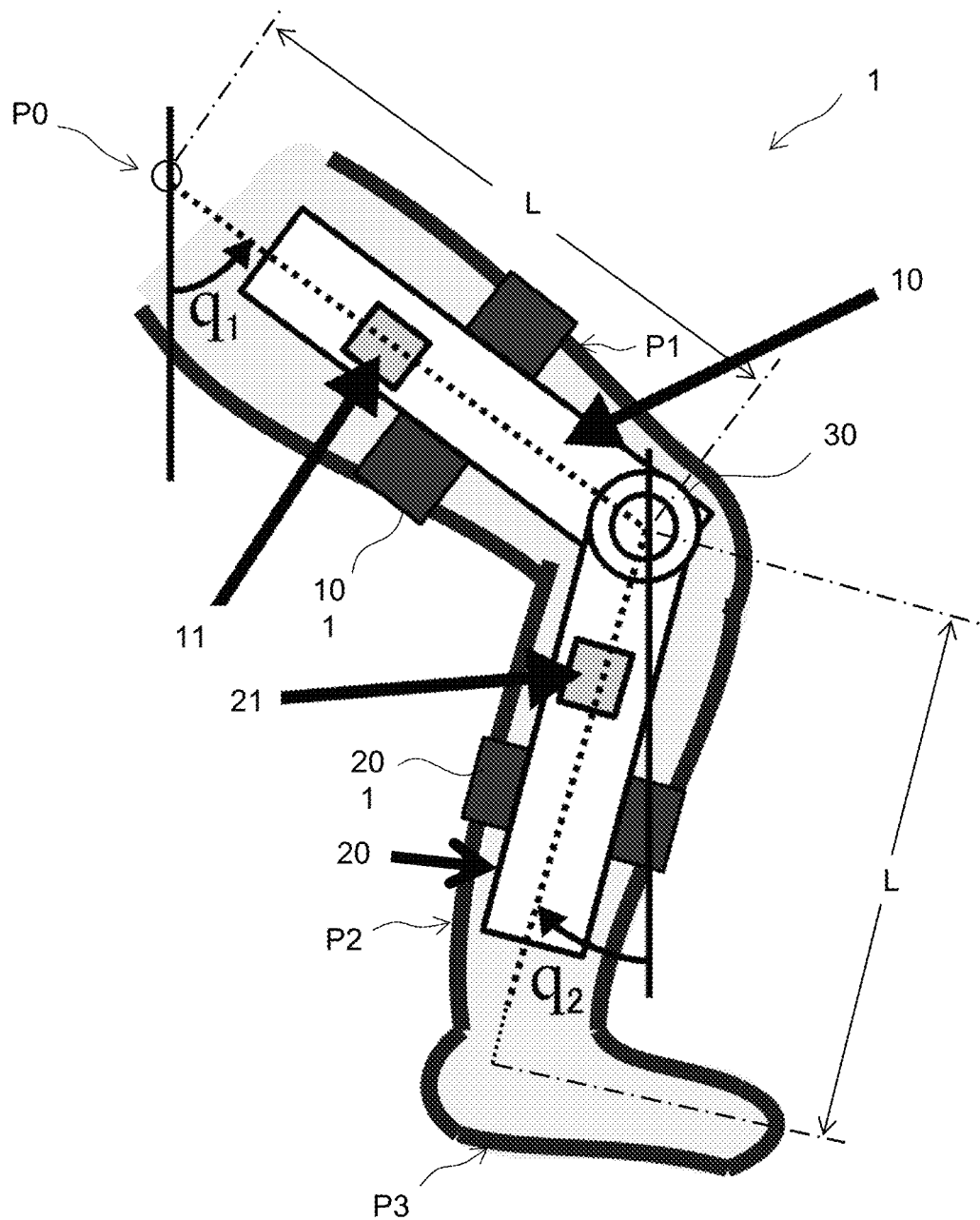
FIG. 1 schematically shows one embodiment of a walking assistance attachment in a walking assistance apparatus according to the present invention, which omits a part of a variable stiffness mechanism.

FIG. 1 schematically shows one embodiment of a walking assistance attachment in a walking assistance apparatus according to the present invention. For the purpose of illustration, FIG. 1 omits a part of a variable stiffness mechanism 4, and FIGS. 2A and 2B show the details of this variable stiffness mechanism 4.

Figure 2A:
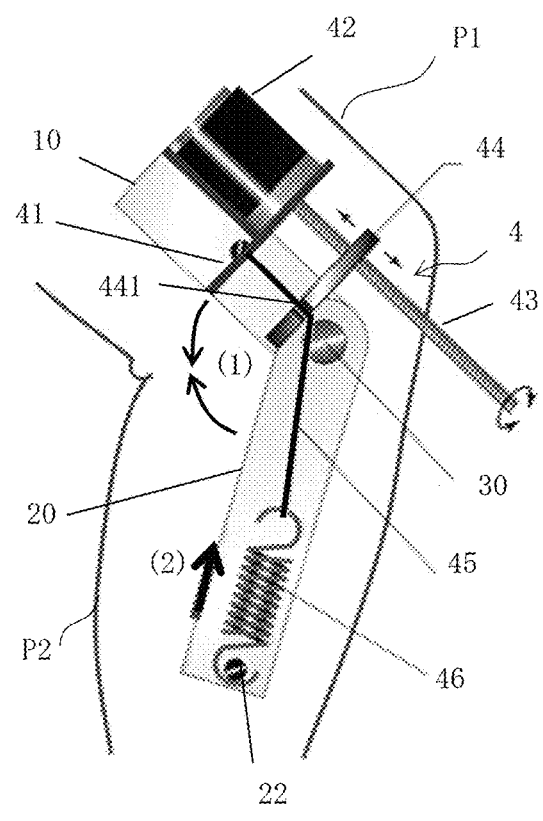
FIG. 2A explains the configuration and the operation of the variable stiffness mechanism, showing the variable stiffness mechanism in a swing-leg state.
Figure 2B:
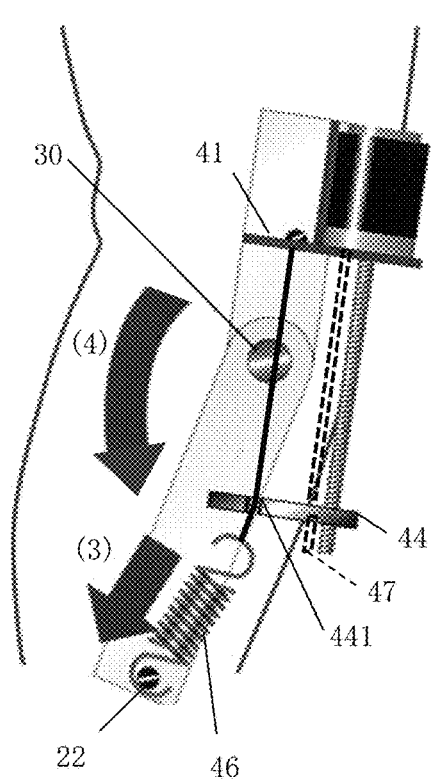
FIG. 2B explains the configuration and the operation of the variable stiffness mechanism, showing the variable stiffness mechanism in a stance-leg state.

The walking assistance apparatus includes a walking assistance attachment 1 in FIG. 1 and the variable stiffness mechanism 4 in FIGS. 2A and 2B. The operation of the variable stiffness mechanism 4 is controlled by a controller 5 in FIG. 3.

In FIG. 1, the walking assistance attachment 1 includes an upper link 10 and a lower link 20 that have a plate shape and are coupled mutually swingably at their respective one ends via a rotating member 30. The upper link 10 and the lower link 20 are made of a rigid material, and have the lengths corresponding to the lengths of a thigh P1 and a lower thigh P2 of a human, respectively. The lengths of the upper link 10 and the lower link 20 may have the same dimension (L) as in the present embodiment, or may have the dimensions corresponding to the size of the body of a user who wears the attachment (e.g., P1 has the length L1 and P2 has the length L2). P0 denotes an appropriate position of the user's trunk, which is a part of the waist in the present embodiment. P3 denotes a part of the foot end.

At around a mid-part of the upper link 10 and the lower link 20, binding belts 101 and 201 are attached, respectively, which are one example of a binder. These binding belts 101 and 201 are wound around the thigh P1 and the lower thigh P2, respectively, so as to fasten the upper link 10 and the lower link 20 to the outer lateral face of the leg for fixing. Such binding operation is performed while positioning the rotating member 30 at a lateral part of the knee. Therefore, when the user wears the walking assistance attachment 1, the upper link 10 and the lower link 20 swing about the rotating member 30 as the user bends and stretches the thigh P1 and the lower thigh P2. Instead of the belt, a band, a hook and loop fastener, and mechanical fastening members may be used as the binder.

Attitude sensors 11 and 21 are attached at appropriate positions of the upper link 10 and the lower link 20, respectively, e.g., at around mid-parts in their longitudinal directions. The attitude sensors 11 and 21 may be an acceleration sensor or a gyro sensor. The attitude sensor 11 is to detect an inclination angle q1 relative to the vertical direction of the upper link 10, i.e., the thigh P1. The attitude sensor 21 is to detect an inclination angle q2 relative to the vertical direction of the lower link 20, i.e., the lower thigh P2.

FIGS. 2A and 2B explain the configuration and the operation of the variable stiffness mechanism 4. FIG. 2A shows the swing-leg state where the leg is floating over the ground, and FIG. 2B shows the stance-leg phase where the leg is in contact with the ground. The variable stiffness mechanism 4 is mounted on the walking assistance attachment 1. The variable stiffness mechanism 4 is attached to the upper link 10 and the lower link 20. In the present embodiment, a plate-shaped attachment member 41 is disposed perpendicularly to the lateral face of the upper link 10, and a motor 42 as a driving source is fixed to the attachment member 41. The motor 42 has an output shaft, to which a ball screw 43 having a predetermined length is coupled so that the ball screw 43 rotates normally or reversely as the motor 42 drives. The motor 42 is attached to the attachment member 41 so that the axial direction of the ball screw 43 extends toward the rotating member 30 and is preferably parallel to the longitudinal direction of the upper link 10.

A nut 44 functions as a movable supporting member as described below. The nut 44 has an internally-threaded hole, with which the ball screw 43 is screwed. As shown in FIG. 2B (omitted in FIG. 2A for the purpose of illustration), a rod body 47 for regulating rotation is disposed perpendicularly to the attachment member 41 and is parallel to the ball screw 43. The nut 44 has an engagement hole or notch to regulate the rotating operation only with the rod body 47. Therefore, when the motor 42 rotates while the nut 44 being screwed with the ball screw 43, the nut 44 engages with the rod body 47 and is regulated in rotation. As a result, the nut 44 reciprocates between the proximal end and the distal end of the ball screw 43 as the motor 42 rotates normally and reversely. FIG. 2A shows the state where the nut 44 is positioned close to the proximal end, and FIG. 2B shows the state where the nut 44 is positioned close to the distal end.

At an appropriate position of the attachment member 41, one end of wire 45 is tied. The wire 45 has a predetermined length, and the other end of the wire 45 engages with one end of an elastic member such as a spring, preferably a linear spring 46 having a predetermined elastic coefficient.

On the lateral face of the lower link 20, a latching part 22 is disposed at an appropriate position on the opposite side of the rotating member 30 attached. The proximal end of the linear spring 46 is latched with the latching part 22. The wire 45 engages with the nut 44 to define a detour. Specifically, the wire 45 passes through a through hole 441 bored in the nut 44 in the thickness direction. In a preferable embodiment, when the nut 44 reciprocates, the through hole 441 faces the rotating member 30 on the way of the moving. When lower thigh P2 bends relative to thigh P1 around the knee joint, the linear spring 46 swings around the through hole 441 together with the wire 45. Hereinafter the position of the through hole 441 is referred to as a supporting point 441 of the swinging of the linear spring 46. During the swing phase in FIG. 2A, the supporting point 441 is positioned close to the rotating member 30 (i.e., the knee), preferably positioned on the proximal side that is close to the upper link 10 relative to the rotating member 30. In FIG. 2B, the supporting point 441 is positioned away from the rotating member 30 (i.e., the knee) toward the distal end. When lower thigh P2 bends relative to thigh P1 as in the swing phase of FIG. 2A, the supporting point 441 is positioned close to the knee, and the linear spring 46 extends to some extent, i.e., the linear spring 46 generates a weak force. Then, when at least one of the upper link 10 and the lower link 20 bends further from the state of FIG. 2A (see arrow (1)), since the distance from the supporting point 441 to the latching part 22 hardly changes, the attachment keeps such low stiffness (see arrow (2)). This enables a smooth swinging motion of the leg during the swing phase, which leads to a natural walking motion.

During the stance phase in FIG. 2B, the supporting point 441 is positioned close to the distal end relative to the knee, and the linear spring 46 extends by the length corresponding to the detouring (increased length of the detour) of the supporting point 441 relative to the length of the line between the rotating member 30 and the latching part 22. That is, the linear spring 46 generates a strong force and has high elastic energy. If the motion occurs to bend lower thigh P2 in this state, such a bending motion is prevented because of the strong force of the linear spring 46. That is, the attachment assists the stance leg so as to avoid knee bending due to its high stiffness. Further, the high elastic energy of the linear spring 46 in this state (see arrow (3)) acts as a strong returning force to return the lower link 20 in the direction parallel to the upper link 10 (see arrow (4)). Therefore the user can easily perform a shifting motion from the swing phase to the stance phase and can easily avoid knee bending during the stance phase because they can use this force as an assisting force. Especially this is preferable when the user shifts the weight (trunk) to the leg on the stance side or lifts the weight during walking upstairs. Apparently the linear spring 46 In FIG. 2B does not extend from the state of FIG. 2A for the reason of drawing, but the linear spring 46 actually extends more as stated above and shows high stiffness.

Figure 3:
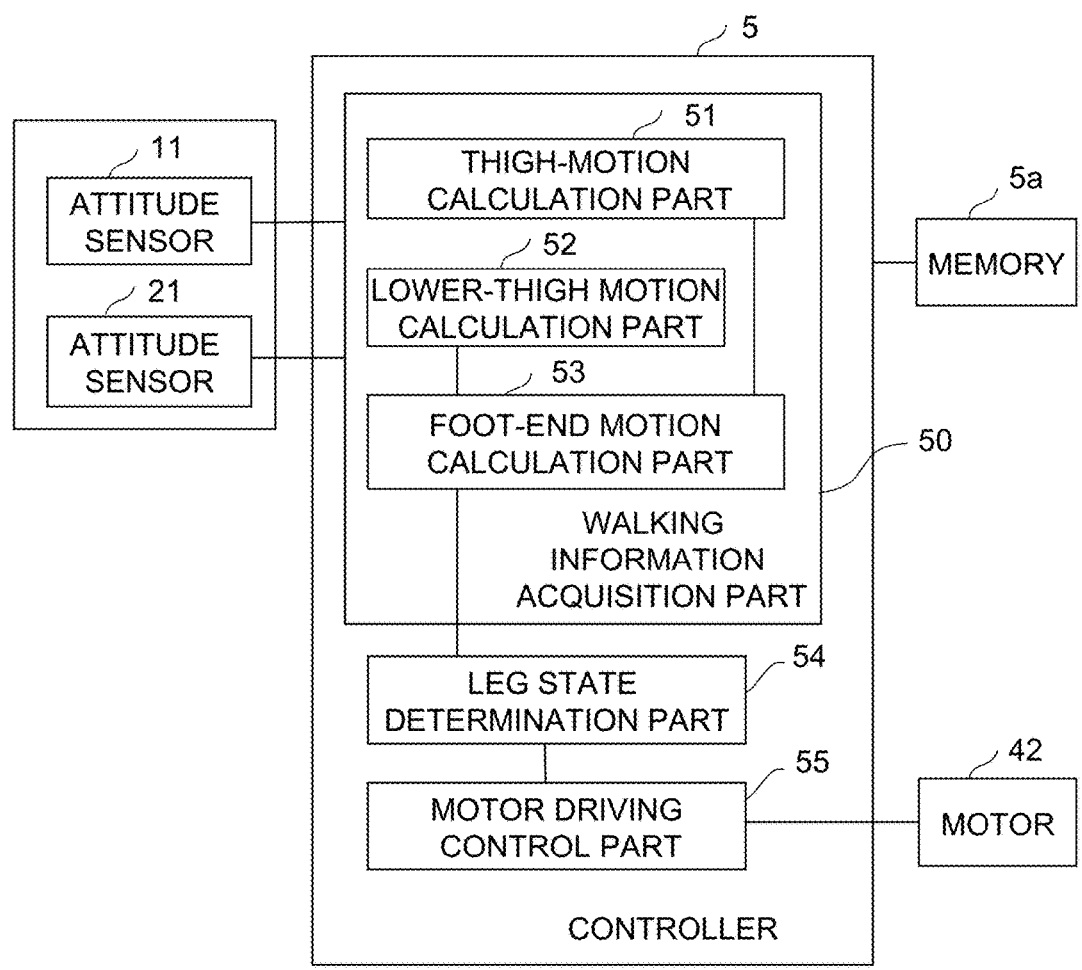
FIG. 3 is a block diagram showing one embodiment of a control system of the walking assistance apparatus according to the present invention.

FIG. 3 is a block diagram showing one embodiment of a control system of the walking assistance apparatus according to the present embodiment. The controller 5 includes a microcomputer or the like in the present embodiment, and is mountable to a waist, a shoulder or a back of the user, for example. The controller 5 includes a processor, and is connected to the attitude sensors 11 and 21, the motor 42 and a memory 5*a*. The memory 5*a* has a memory area in which a processing program or data necessary for the processing are stored, and a work memory area in which data being processed is stored temporarily.

When the processor executes a processing program, the controller 5 functions as a walking information acquisition part 50, a leg state determination part 54 and a motor driving control part 55. The walking information acquisition part 50 is to acquire information on the walking state of a user from the detection result of the attitude sensors 11 and 21. The leg state determination part 54 is to determine the state of the user's leg from the walking information on the user. The motor driving control part 55 is to drive the motor 42 in accordance with the state of the leg. The walking information acquisition part 50 includes a thigh-motion calculation part 51, a lower-thigh motion calculation part 52 and a foot-end motion calculation part 53.

The thigh-motion calculation part 51 successively fetches the motion of thigh P1 from the attitude sensor 11 with a predetermined period. The thigh-motion calculation part 51 calculates the inclination angle q1 relative to the vertical direction of the upper link 10 from the detected signals that are successively fetched from the attitude sensor 11, and calculates an angular velocity Vq1 from the successive inclined angles q1.

The lower-thigh motion calculation part 52 successively fetches data from the attitude sensor 21 with a predetermined period. The lower-thigh motion calculation part 52 calculates the inclination angle q2 relative to the vertical direction of the lower link 20 from the detected signals that are successively fetched from the attitude sensor 21, and calculates an angular velocity Vq2 from the successive inclined angles q2.

The foot-end motion calculation part 53 periodically finds a relative velocity Vx of the foot end P3 with reference to the waist P0 of the user. The relative velocity Vx is found from the inclination angle q1 and the angular velocity Vq1 calculated by the thigh-motion calculation part 51, the inclination angle q2 and the angular velocity Vq2 calculated by the lower-thigh motion calculation part 52, and the dimensions L of the thigh P1 and the lower thigh P2 (in the case of L1=L2) by the following expression:

$$Vx = L \cdot \cos(q1) \cdot Vq1 - L \cdot \cos(q2) \cdot Vq2 \qquad \text{(Exp. 1).}$$

In Exp. 1, a position in the walking direction relative to (forward of) the waist P0 is positive, and the velocity in the walking direction with reference to the velocity of the waist P0 is positive.

The foot-end motion calculation part 53 successively calculates a relative position of the foot end with reference to the waist P0 of the user from the velocity Vx.

The leg state determination part 54 determines the grounding timing of the foot end P3 based on the polarity of Vx that is successively calculated, that is, based on the positive/negative changing state of Vx. Since the polarity of Vx does not change with the dimension L, the length of the leg does not relate to the determination of the grounding timing. That is, the grounding timing can be determined even when the length of the leg is unknown. The motor driving control part 55 outputs a driving instruction to the motor 42 in accordance with the determination result of the leg state determination part 54.

Figure 4:
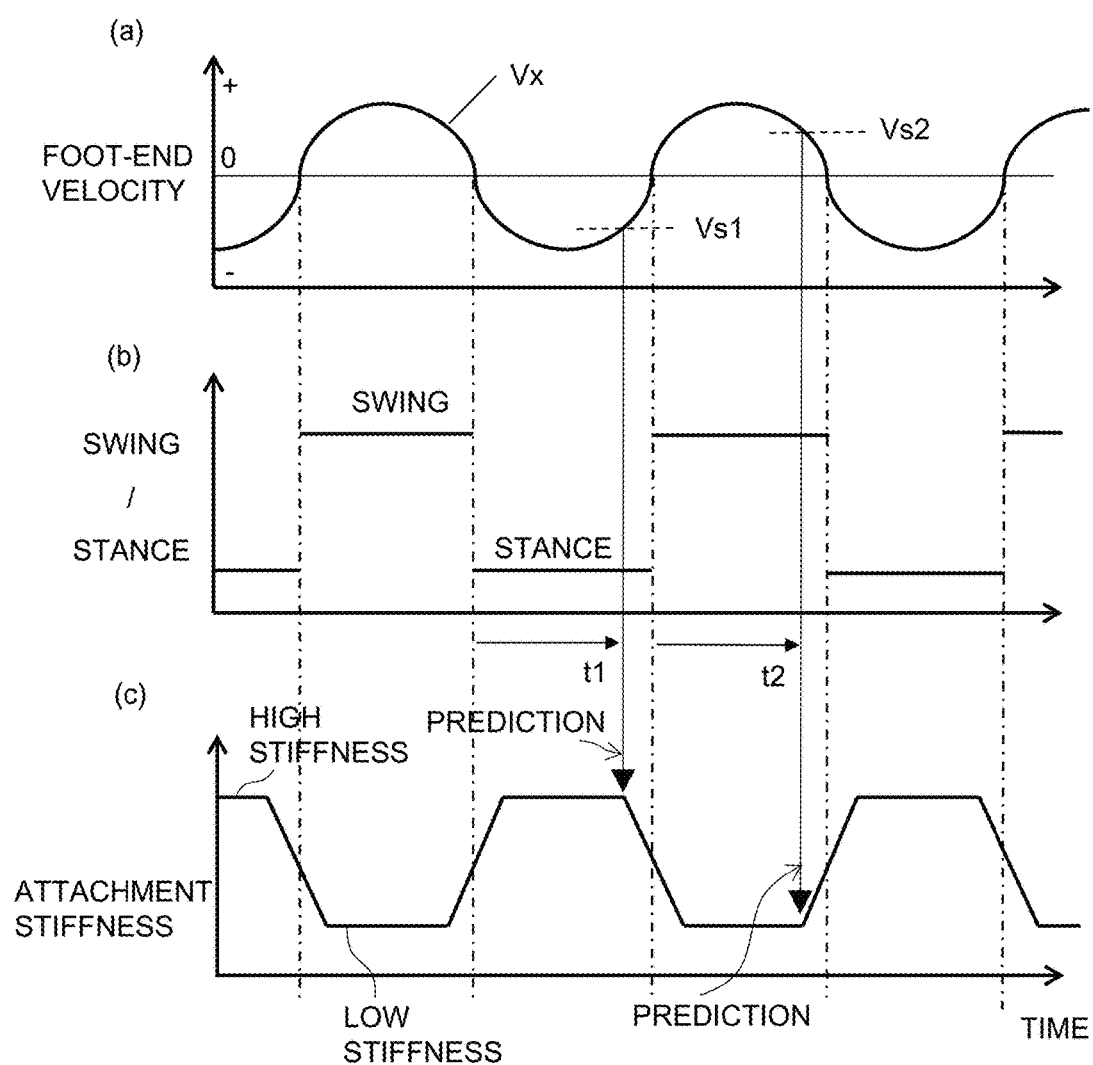
FIG. 4 is a time chart of the states of a leg and signals corresponding to the walking motion.

Referring to the time chart of FIG. 4, the following describes the relationship between the state of one leg during the walking motion and controlling of the motor driving. As shown in "swing/stance" in FIG. 4(*b*), walking of a human (including walking upstairs/downstairs) includes the motion of leaving a grounded leg from the ground behind the waist (starting of a swing phase), moving that leg forward in the travelling direction, and grounding the leg at a position in front of the waist (ending of the swing phase). From this timing, a stance phase of the leg starts. During this stance phase, the other leg is left from the ground behind the waist in a similar manner, is moved forward, and is grounded. Then, such motions are repeated. One swing phase and one stance phase correspond to the time of walking in one step.

As shown in the "foot-end velocity" of FIG. 4(*a*), the velocity Vx of the foot end P3 relative to the waist P0 changes from negative to positive when starting the bending of one leg to leave the leg from the ground (starting of a swing phase). Then, after shifting to the swing phase, Vx increases as the leg is moved forward of the body. Next, as the leg gets closer to the ground, Vx decreases. Vx=0 when the leg is grounded (ending of the swing phase). While the leg is grounded, the other leg moves as stated above to move the body forward. As a result, the velocity Vx of the grounded leg is negative, and shows characteristics similar to the above.

Based on the features of human's walking as stated above, the relationship among the swing phase/stance phase and the relative foot-end position and velocity is as follows. That is, when the target leg has a positive value of the velocity Vx, the leg is in the swing phase. When the target leg has a negative value of the velocity Vx, it is in the stance phase. Since the velocity Vx changes continuously and also has periodicity, the walking state can be predicted. Herein, also when the foot-end of the target leg is positioned forward (positive) of the waist P0, the leg shifts from the swing phase to the stance phase. When the foot-end of the target leg is positioned backward (negative) of the waist P0, the leg shifts from the stance phase to the swing phase. Such a condition can be used as additional information to determine the walking state. Walking fast and running also may be included in the same mode as the walking as long as they have the features similar to those of the walking.

"Stiffness of attachment" in FIG. 4(*c*) shows the setting of the supporting point 441 by the motor 42. That is, stiffness of the attachment is changed from low stiffness to high stiffness in response to the shift from the swing phase to the stance phase, and is changed from high stiffness to low stiffness in response to the shift from the stance phase to the swing phase. The timing of shifting between the swing phase and the stance phase can be predicted by obtaining detected signals of the attitude sensors 11 and 21 successively and calculating the foot-end velocity Vx successively. That is, it can be determined that the leg phase has shifted from the stance phase to the swing phase at the time when the foot-end velocity Vx has a negative value and the value Vx becomes a predetermined threshold Vs1 close to 0 (time t1 immediately before the time of Vx=0). On the other hand, it can be determined that the leg phase has shifted from the swing phase to the stance phase at the time when the foot-end velocity Vx has a positive value and the value Vx becomes a predetermined threshold Vs2 close to 0 (time t2 immediately before the time of Vx=0). At such timing, stiffness of the attachment is changed transiently. In the example of FIG. 4, stiffness is changed transiently across the time corresponding to the velocity Vx=0. For the values of high and low stiffness and the transient duration, their preferable characteristic values can be obtained by setting them experimentally or empirically, for example. Although stiffness may be changed for a short time, changing of the stiffness transiently allows a smooth and more natural walking motion including grounding and leaving from the ground as compared with the changing for a short time. Torque applied to the motor 42 also can be suppressed, and so electric power can be saved.

Figure 5:
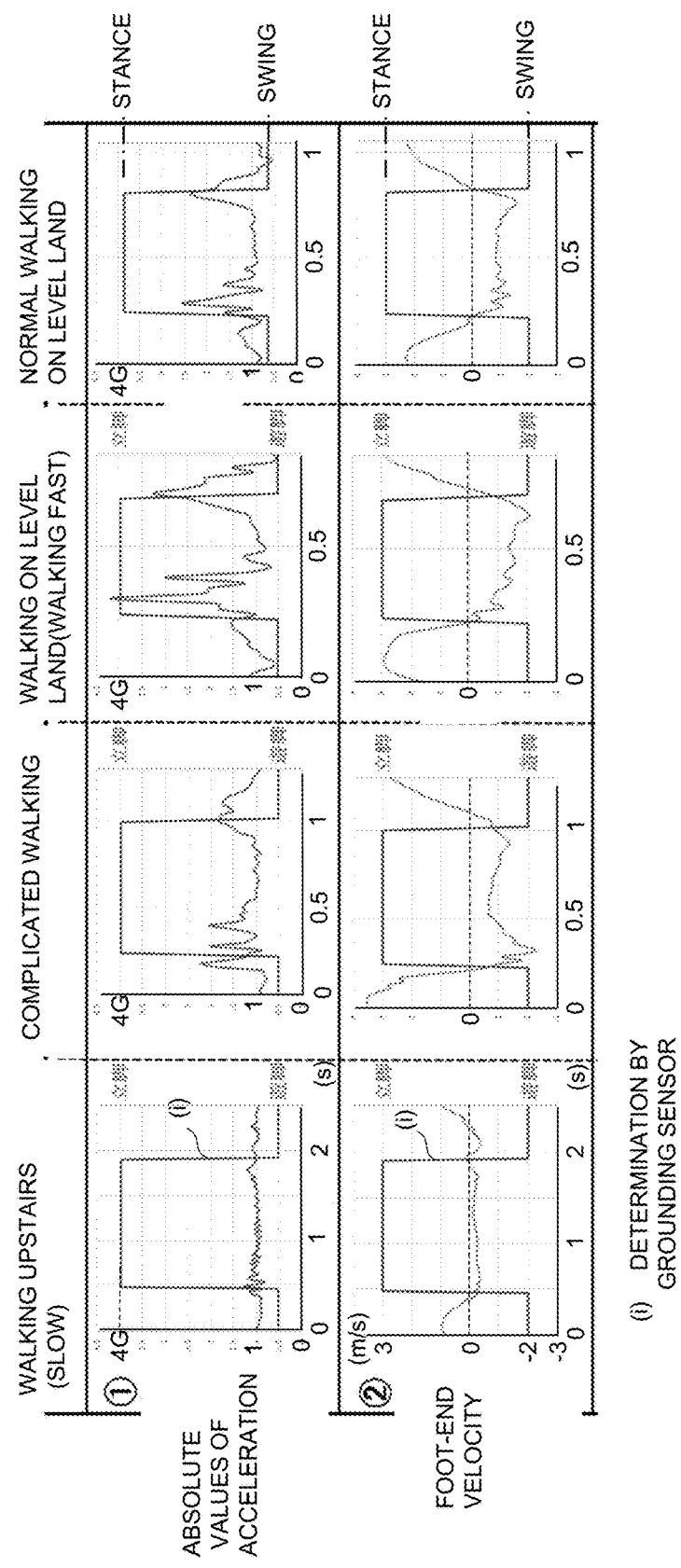
FIG. 5 is a waveform chart showing the result of an experiment to explain the evaluation on determination of leg-phase shifting using the attitude sensors according to the present embodiment.

FIG. 5 is a waveform chart showing the result of an experiment to explain the evaluation on determination of leg-phase shifting using the attitude sensors 11 and 21 according to the present embodiment. Whether the leg is grounded or not is indicated with a detection signal (square wave form (i) of the stance leg and the swing leg in the chart) of a grounding sensor attached to the sole. In FIG. 5, the upper part shows a comparative example corresponding to Patent Literature 8 (Japanese Patent Application Laid-Open No. 2008-175559), and in this example, leg-phase was determined based on the absolute values of acceleration. The lower part shows the present example including the mechanism shown in FIG. 1 having the attitude sensors 11 and 21. For the attitude sensors 11 and 21, a sensor TSND121 (produced by ATR-Promotions company) was used, including a triaxial gyro and a triaxial acceleration sensor therein. The detection period was 50 times/sec.

The walking modes include "normal walking on level land" on the right end, and other walking modes of "walking on level land (walking fast)", "complicated walking" and "walking upstairs (slow)" that are shown in this order toward the left. In FIG. 5, in the case of "normal walking on level land", acceleration at a predetermined level was successfully detected so as to correspond to the leg-phase shifting in the comparative example of the upper part. Therefore it seems that the leg-shift timing can be determined in this case in the comparative example. In the present example of the lower part, since there is matching with positive/negative values of the relative velocity of the foot end, the leg-shift timing can be determined in the present example.

On the contrary, when the walking speed was changed in the comparative example of the upper part as in "walking on level land (walking fast)", it was difficult to set a threshold for determination because the maximum peak of the detected acceleration was greatly changed. This requires the collection of data corresponding to one step to determine the maximum peak, and so real-time processing is difficult. In the case of "complicated walking" including components of individual differences in walking, walking upstairs/downstairs, shifting from walking to walking upstairs/downstairs, walking along a crooked road, and walking while changing the velocity rapidly, many peaks having different values of acceleration were generated, and it was very difficult to determine leg-phase shift timing between stance legs and swing legs. In the case of "walking upstairs (slow)", it was difficult to seta threshold for detection of a peak.

On the other hand, in the present example of the lower part, matching with positive/negative values of the relative velocity of the foot end was obtained in all of the walking modes without the need of a sensor on the sole, and therefore the leg-shift timing can be determined in the present example. This shows that the present example enables determination of leg-phase shift timing using the positive/negative polarity of the relative velocity of a foot end, or a changing state from positive to negative or from negative to positive.

Figure 6:
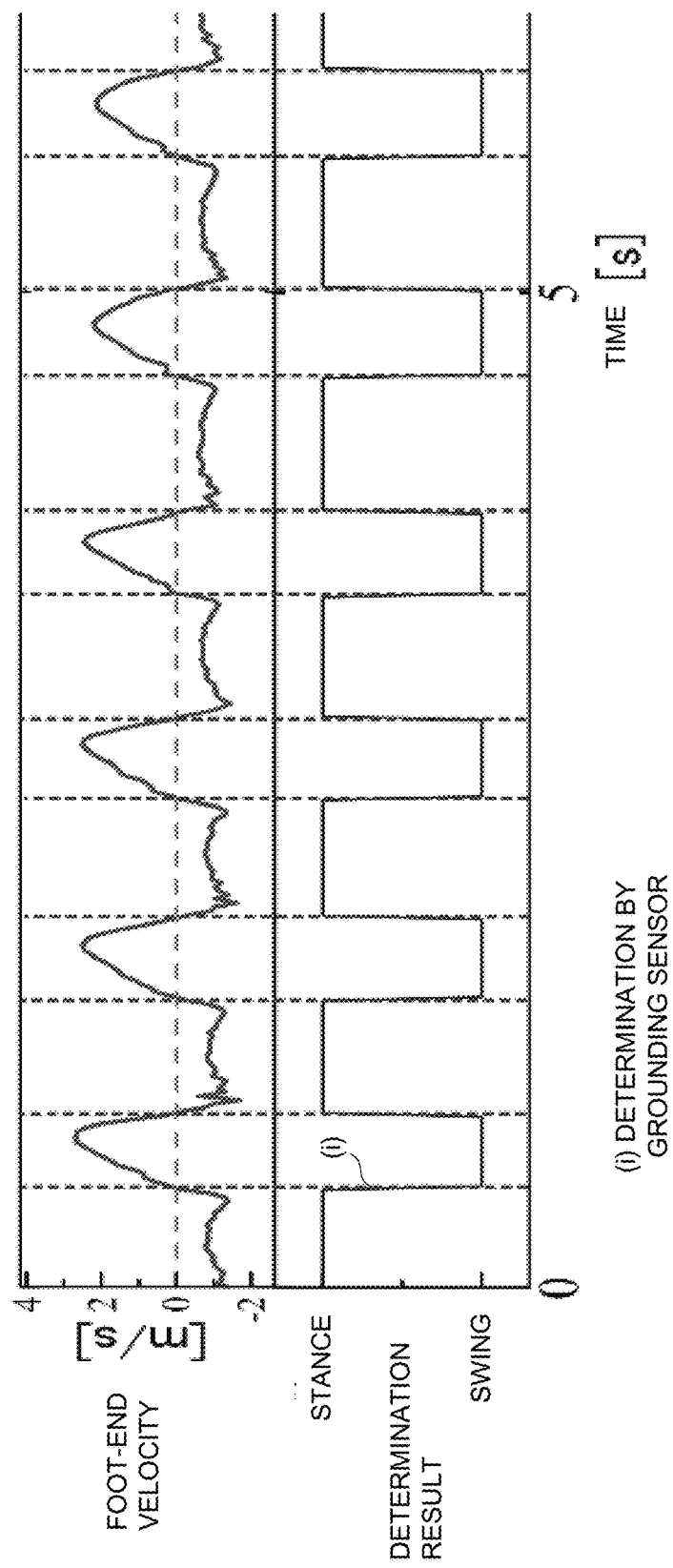
FIG. 6 is a time chart showing the result of an experiment to compare the relative velocity of a foot end with the state of the stance leg and the swing leg using the mechanism of FIG. 1.

FIG. 6 is a time chart showing the result of an experiment to compare the relative velocity of a foot end with the state of the stance leg and the swing leg using the mechanism of FIG. 1. In FIG. 6, the walking speed of each left/right step is a normal walking speed (period), e.g., one left/right step/sec. The upper part of FIG. 6 shows the relative velocity of the foot end, and the lower part shows a square wave form (i) of the stance leg and the swing leg using a grounding sensor. As is evident from the chart, when the relative velocity of the foot end is about to change from negative to positive, the leg phase is at the stage of shifting from the stance phase to the swing phase. Conversely, when the relative velocity of the foot end is about to change from positive to negative, the leg phase is at the stage of shifting from the swing phase to the stance phase. Therefore the positive/negative polarity of the relative velocity of the foot end matches with the shift timing between the stance leg and the swing leg.

Figure 7:
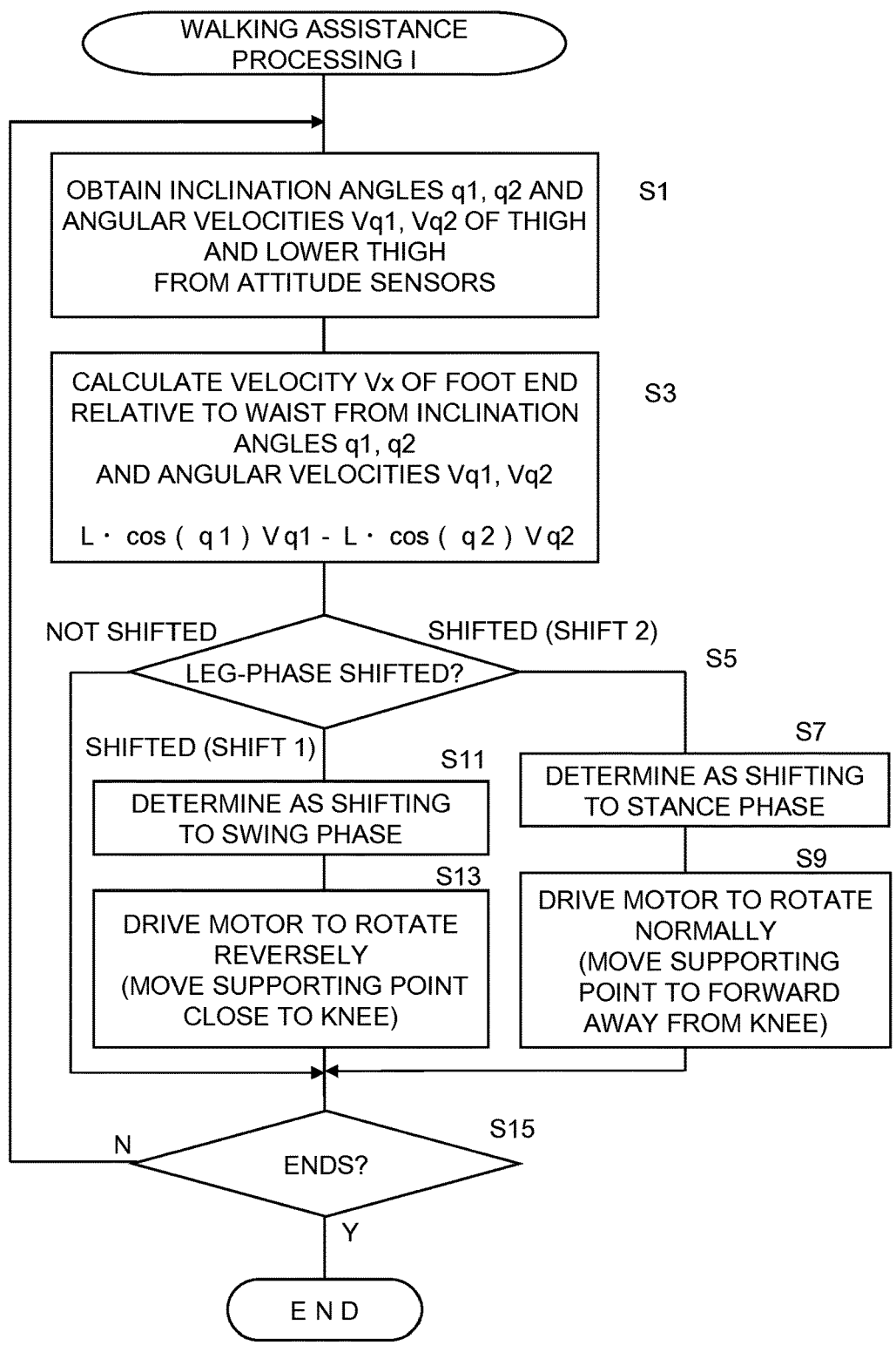
FIG. 7 is a flowchart showing the walking assistance processing I.

FIG. 7 is a flowchart showing the processing I that is one example of the walking assistance processing. In this flowchart, inclination angles q1, q2 and angular velocities Vq1, Vq2 are obtained from the detected signals of the attitude sensors 11 and 21 (Step S1). Next, velocity Vx of the foot end relative to waist P0 is calculated from the inclination angles q1, q2 and the angular velocities Vq1, Vq2 (Step S3). Then, determination is made whether the leg phase has shifted or not (Step S5).

In the mode of changing stiffness for a short time, this determination can be made at the timing when velocity Vx changes across 0.

On the other hand, when the determination at Step S5 is made based on prediction as in the present embodiment, every time velocity Vx is calculated, the polarity of the velocity is determined and the velocity Vx is compared with the threshold Vs1 or Vs2 depending on the polarity. When it is determined that the leg-phase has not shifted, the procedure returns to Step S1 via Step S15, and similar processing is repeated at a predetermined period. When it is determined at Step S5 that the leg-phase has shifted, determination is made whether the shifting is "shift 1" or "shift 2". Such a determination between "shift 1" and "shift 2" may be made based on the polarity of velocity Vx. As stated above, polarity information on the position of the foot end relative to waist P0 that is calculated in addition to the calculation of velocity Vx may be used additionally to make a determination between "shift 1" and "shift 2". Herein "shift 1" refers to the case where relative velocity Vx of the foot end is negative in polarity and the leg-phase shifts from the stance phase to the next swing phase. "Shift 2" refers to the case where relative velocity Vx of the foot end is positive in polarity and the leg-phase shifts from the swing phase to the next stance phase.

When the shifting of leg-phase is determined as "shift 2", then it is determined as shifting to the stance phase (Step S7). Then an instruction is issued to drive the motor 42 to rotate normally with a predetermined amount and at a predetermined velocity (Step S9). When the shifting of leg-phase is determined as "shift 1", then it is determined as shifting to the swing phase (Step S11). Then an instruction is issued to drive the motor 42 to rotate reversely with a predetermined amount and at a predetermined velocity (Step S13). Next, determination is made whether the processing ends or not. If it does not end, the processing as stated above is repeated. When it ends, the procedure leaves this flow.

Figure 8:
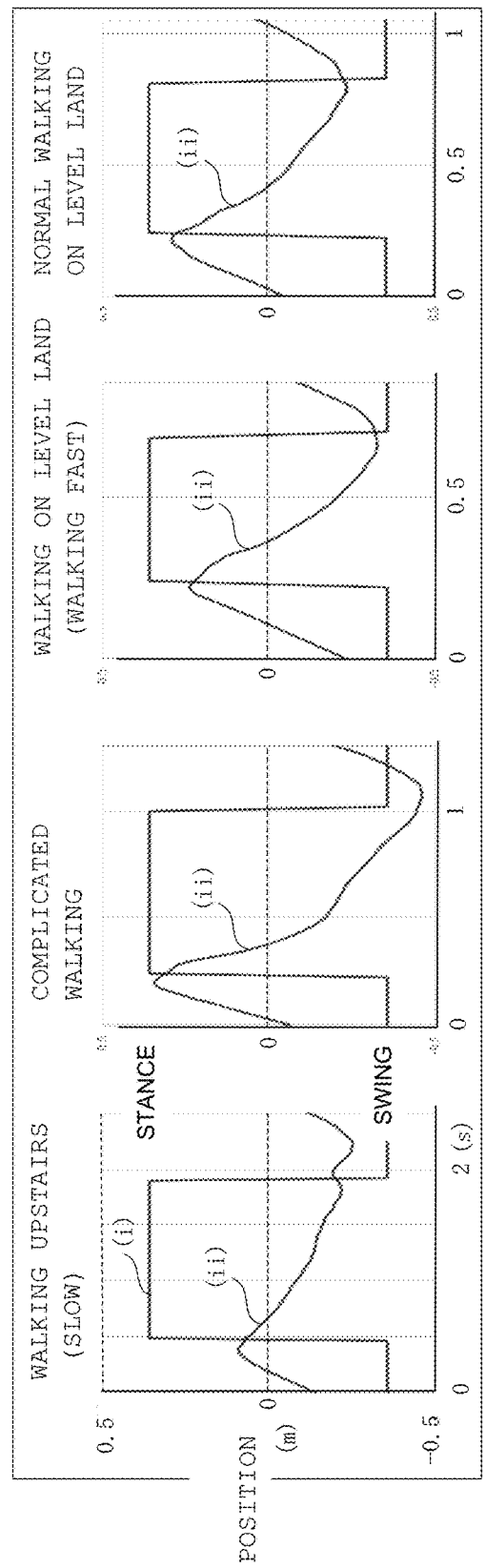
FIG. 8 shows the result of an experiment to evaluate the matching between "shift 1" or "shift 2" and the positive/negative information on the relative position of the foot end.

FIG. 8 shows the result of an experiment to evaluate matching between "shift 1" or "shift 2" and the positive/negative information on the relative position of the foot end. The waveform (ii) shows a relative position obtained from the relative velocity of the foot end. In this drawing, the walking modes of "normal walking on level land", "walking on level land (walking fast)", "complicated walking" and "walking upstairs (slow)" are shown in this order from the right. As shown in all of the modes, at the time of "shift 1", that is, when the leg-phase shifts from the stance phase to the swing phase, the relative position of the foot end is at a negative position. At the time of "shift 2", that is, when the leg-phase shifts from the swing phase to the stance phase, the relative position of the foot end is at a positive position. Therefore it is effective to use the relative velocity of the foot end to determine the shift timing of the leg phase and to use the positive/negative information on the relative position of the foot end to make a determination between "shift 1" and "shift 2".

Figure 9:
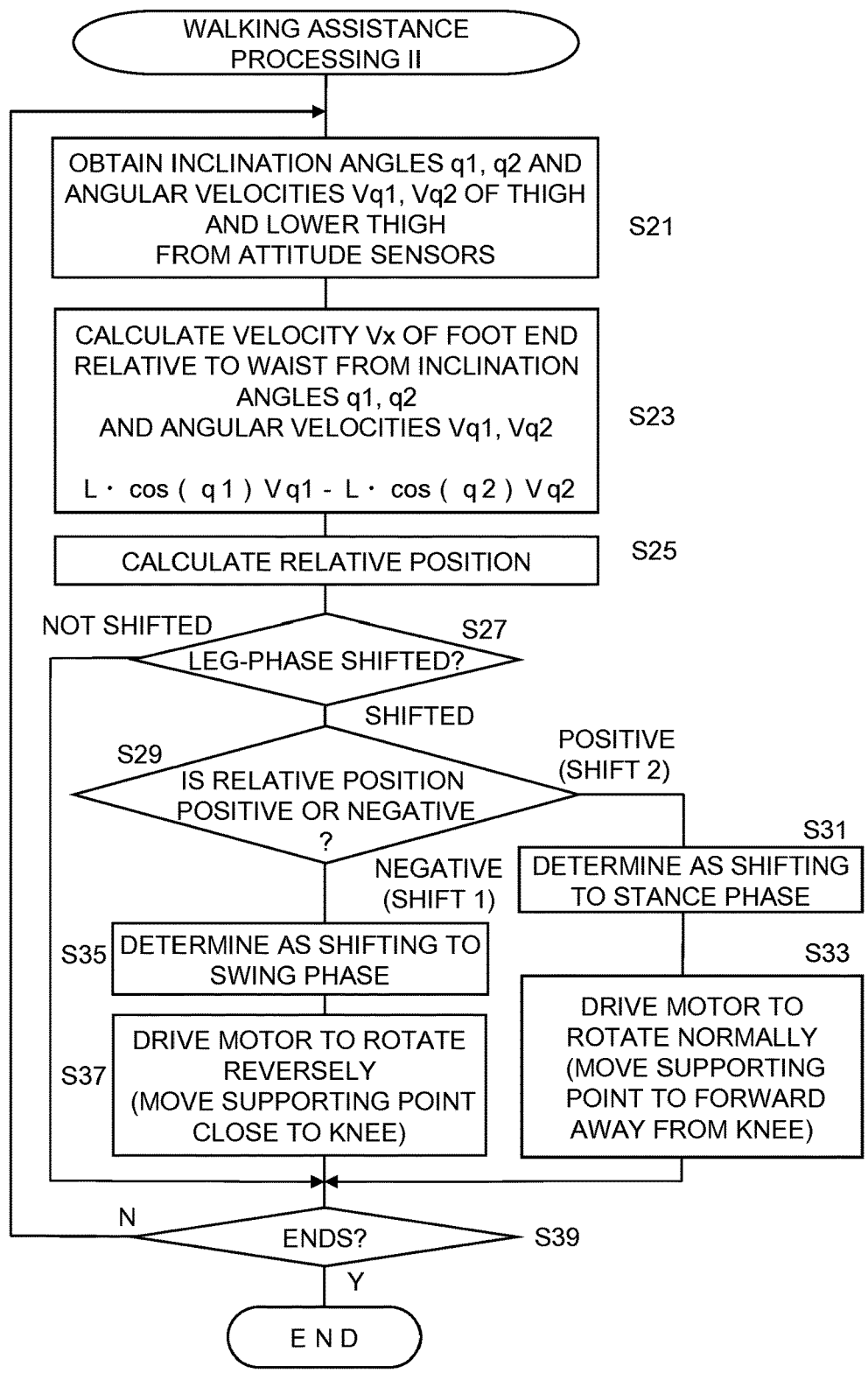
FIG. 9 is a flowchart showing the walking assistance processing II.

FIG. 9 is a flowchart showing the processing II that is another embodiment of the walking assistance processing. In the processing II, determination between "shift 1" and "shift 2" is made based on the exemplary experiment of FIG. 8 and using positive/negative information on the relative position instead of positive/negative information on the relative velocity. In this flowchart, since Steps S21 and S23 are the same as Steps S1 and S3, their descriptions are omitted. Next, at Step S25, the foot-end motion calculation part 53 calculates the relative position of the foot end with reference to waist P0 of the user from the velocity Vx by successive integration, for example.

Next, determination is made whether the leg-phase has shifted or not (Step S27). At Step S27, processing similar to that at Step S5 is performed. That is, every time velocity Vx is calculated, the polarity of the velocity is determined and the velocity Vx is compared with the threshold Vs1 or Vs2 depending on the polarity. When it is determined that the leg-phase has not shifted, the procedure returns to Step S21 via Step S39, and similar processing is repeated at a predetermined period. When it is determined at Step S27 that the leg-phase has shifted, determination is made whether the shifting is "shift 1" or "shift 2" using the polarity information of the relative position of the foot end with reference to waist P0 obtained at Step S25 (Step S29).

When the relative position is positive, then it is determined that shifting of leg-phase is determined as "shift 2", that is, shifting to the stance phase (Step S31). Then an instruction is issued to drive the motor 42 to rotate normally with a predetermined amount and at a predetermined velocity (Step S33). When the relative position is negative, then it is determined that shifting of leg-phase is determined as "shift 1", that is, shifting to the swing phase (Step S35). Then an instruction is issued to drive the motor 42 to rotate reversely with a predetermined amount and at a predetermined velocity (Step S37). Next, determination is made whether the processing ends or not. If it does not end, the processing as stated above is repeated. When it ends, the procedure leaves this flow.

The present invention may be implemented in the following embodiments.

(1) In the embodiment as stated above, the prediction timing to change stiffness is based on the thresholds Vs1 and Vs2. In another embodiment, considering the periodicity of walking, elapsed time from the time corresponding to Vx=0, for example, may be used (e.g., t1, t2 in FIG. 4).

(2) The driving speed and the driving amount of the motor 42 to change stiffness may be adjusted depending on users. Walking modes may be distinguished between walking on the level land and walking upstairs/downstairs by analyzing a detection signal of the attitude sensors, or they may be selected manually using a manipulation unit. Then, the driving speed and the driving amount of the motor 42 to change stiffness may be adjusted in accordance with the walking mode.

(3) The configuration of the variable stiffness mechanism 4 may be changed as follows. For instance, the linear spring 46 may not be linear as long as it has elasticity. Instead of the linear spring 46, an elastic wire rod may be used. Wire may be coupled to each end of the linear spring 46. Instead of the motor 42, another driving source such as an electromagnetic solenoid may be used. Considering the weight of the motor 42, the motor is preferably attached to the upper link 10. Alternatively, the motor 42 may be disposed at the lower link 20, and the ball screw 43 may be rotated reversely from the embodiment as stated above. Instead of the mechanism of the ball screw 43, a sliding screw mechanism and other general mechanisms to convert a rotating motion to a translation motion may be used.

(4) The embodiment as stated above includes the variable stiffness mechanism 4 shown in FIGS. 2A and 2B. The mechanism is not limited to the configuration in FIGS. 2A and 2B as long as it can change stiffness in accordance with the leg-phase of walking. For instance, in another embodiment, stiffness may be changed by variably giving a rotational load to the rotating member 30. The rotational load may be changed by a technique used for an electromagnetic brake or a braking technique of mechanically changing the frictional force.

(5) The attitude sensors 11 and 21 may be configured to measure the angle on the vertical plane using an acceleration sensor, a gyro sensor and other magnetic sensors. In another embodiment, a detection signal of one of the attitude sensors 11 (21) and an interlink angle that can be measured using a rotation sensor disposed at the rotating member 30 may be used. The types and the number of sensors also are not limited as long as they can measure the foot-end velocity (foot-end position) relative to the reference part of the user, typically an appropriate part of the trunk.

(6) The attitude sensors 11 and 21 may be attached to one leg of the human body. This can eliminate the necessity of a pressure sensor on the sole, can reduce restrictions on the motion and can lengthen the life of the sensors. Since both legs are moved alternately, the motion on the other leg can be known from information on the motion of one leg, and accordingly the number of sensors can be reduced. The attachment may be attached not only to one leg but also to both legs. When the attachment is attached to both legs, no attitude sensor is disposed on the walking assistance attachment on the other leg, and the leg phase, the foot-end velocity and the foot-end position of the other leg may be calculated by the controller 5 based on the attitude sensor on the walking assistance attachment on the base leg.

(7) In the embodiment as stated above, the foot-end velocity is specified on the orthogonal coordinate system. The coordinate system is not limited to the orthogonal coordinate system as long as it can evaluate whether the foot-end moves forward or backward of the body. For instance, the foot-end velocity may be specified on the polar coordinates including the waist as the origin. Since cos(q1) and cos(q2) in Exp. 1 always become values close to 1 during walking, approximate calculation such as Vx=L·Vq1−L·Vq2 may be performed.

The thus configured present invention can have a longer life than the configuration including a grounding sensor attached to the sole. Unlike a pressure sensor such as the grounding sensor, motion information can be obtained successively, and therefore the motion in the future can be predicted. Due to such prediction of the motion in the future, the configuration of the present invention can have higher assisting efficiency than the conventional configurations, and can be used to develop a robotic orthosis or prosthetic leg that enables natural assisting. This can be used to an attachment of a type that cannot be attached to the sole. Wearing and removing of the attachment also is easy, and so the attachment has excellent operability and user-friendliness.

The processing to determine the leg-phase shift timing between swing phase and stance phase by the controller 5 is not limited to the application to the variable stiffness mechanism 4. Such processing may be applied to other types of walking assistance apparatuses that use leg-phase shift timing.

As stated above, a leg-phase shift timing determination apparatus according to the present invention includes: a walking information acquisition unit configured to receive an output from a sensor to detect motion of a leg of a human body and successively calculate a relative velocity of a foot end with reference to a reference part of the human body; and a leg state determination unit configured to determine shift timing between a swing phase and a stance phase based on the relative velocity of the foot end.

According to the present invention, the walking information acquisition unit receives an output from a sensor and successively calculates a relative velocity of a foot end with reference to a reference part of the human body, e.g., a waist. Then the leg state determination unit determines shift timing between a swing phase and a stance phase based on the relative velocity of the foot end calculated by the walking information acquisition unit. The shift timing is determined whether it shifts from a swing phase to a stance phase or from a stance phase to a swing phase. Therefore, shift timing between a swing phase and a stance phase can be determined more precisely based on the relative foot-end velocity with reference to the reference part of the human body.

Preferably, in the leg-phase shift timing determination apparatus according to the present invention, the leg state determination unit is configured to determine shift timing between a swing phase and a stance phase based on the relative velocity of the foot end and positive and negative polarities of the relative velocity. With this configuration, positive and negative polarity information on the relative velocity also is used, and therefore shift timing between a swing phase and a stance phase can be determined precisely.

Preferably, in the leg-phase shift timing determination apparatus according to the present invention, the walking information acquisition unit is configured to receive an output from the sensor and successively calculate a relative position of the foot end with reference to a reference part of the human body; and the leg state determination unit is configured to, based on whether the relative position of the foot end is positive or negative, determine whether shift timing is from the swing phase to the stance phase or from the stance phase to the swing phase. With this configuration, positive or negative information on the relative position of the foot-end is additionally used in the determination, whereby leg-phase shift timing can be determined more precisely Preferably, in the leg-phase shift timing determination apparatus according to the present invention, the sensor is configured to detect motion of a thigh and a lower thigh of the human body as the motion of the leg. This configuration can eliminate the necessity of a pressure sensor on the sole, and therefore restrictions on the motion can be reduced, and the life of the apparatus can be lengthened.

Preferably, in the leg-phase shift timing determination apparatus according to the present invention, the relative velocity Vx of the foot end is calculated by the following expression:

$$Vx = L1 \cdot \cos(q1) \cdot Vq1 - L2 \cdot \cos(q2) \cdot Vq2 \qquad \text{(Exp. 2)}$$

In Exp. 2, Vx denotes the relative velocity of the foot end with reference to a waist of the human body, q1 and Vq1 denote an inclination angle and an angular velocity of the thigh, q2 and Vq2 denote an inclination angle and an angular velocity of the lower thigh, and L1 and L2 denote dimensions of the thigh and the lower thigh of the human body.

Preferably in the leg-phase shift timing determination apparatus according to the present invention, the sensor includes at least one type of an acceleration sensor, a magnetic sensor and a gyro sensor. This configuration enables successive acquisition of detection signals, which enables future prediction processing. Since this configuration does not include a sensor attached to the sole, the life of a sensor can be lengthened. The sensor can be attached to one leg only, and sensors on both legs are not required.

The present invention provides a method for determining leg-phase shift timing. The method includes: a walking information acquisition step of receiving an output from a sensor to detect motion of a leg of a human body and successively calculating a relative velocity of a foot end with reference to a reference part of the human body; and a leg state determination step of determining shift timing between a swing phase and a stance phase based on the relative velocity of the foot end calculated at the walking information acquisition step.

Preferably the leg state determination step includes determining shift timing between a swing phase and a stance phase based on the relative velocity of the foot end and positive and negative polarities of the relative velocity.

Preferably, in the method for determining leg-phase shift timing, the walking information acquisition step includes receiving an output from the sensor and successively calculating a relative position of a foot end with reference to a reference part of the human body; and the leg state determination step includes, based on whether the relative position of the foot end is positive or negative, determining whether shift timing is from the swing phase to the stance phase or from the stance phase to the swing phase.

The present invention provides a walking assistance apparatus, and the walking assistance apparatus includes: a walking assistance attachment to be attached to a leg of a human body and including a variable stiffness mechanism having stiffness that is changeable in a direction where the human bends and stretches the knee; the leg-phase shift timing determination apparatus according to the present invention; and a stiffness control unit configured to increase the stiffness of the variable stiffness mechanism at shift timing from the swing phase to the stance phase and to decrease the stiffness of the variable stiffness mechanism at shift timing from the stance phase to the swing phase.

The present invention provides a method for controlling walking assistance for a walking assistance attachment to be attached to a leg of a human body and including a variable stiffness mechanism having stiffness that is changeable in a direction where the human bends and stretches the knee. The method includes: a walking information acquisition step of receiving an output from a sensor to detect motion of the leg and successively calculating a relative velocity of a foot end with reference to a reference part of the human body; a leg state determination step of determining shift timing between a swing phase and a stance phase based on the relative velocity of the foot end calculated at the walking information acquisition step; and a stiffness control step of increasing the stiffness of the variable stiffness mechanism at shift timing from the swing phase to the stance phase and decreasing the stiffness of the variable stiffness mechanism at shift timing from the stance phase to the swing phase.

According to the present invention, the walking assistance attachment is attached to a leg of a human body and the variable stiffness mechanism changes the stiffness to adjust the torque to be given in the direction where the human bends and stretches the knee. For instance, the shift timing between a swing phase and a stance phase of the walking assistance attachment is determined by the leg-phase shift timing determination apparatus having a sensor to detect a motion of the leg. The stiffness control unit increases the stiffness of the variable stiffness mechanism at shift timing from the swing phase to the stance phase and decreases the stiffness of the variable stiffness mechanism at shift timing from the stance phase to the swing phase. In this way, walking states can be determined to find shift timing between a swing phase and a stance phase, and the stiffness can be increased or decreased in accordance with the determination. Thereby the knees can be assisted favorably.

Preferably, the stiffness control unit is configured to keep a set current stiffness until starting time of next shift timing. With this configuration, stiffness required for the duration of the swing phase and the stance phase can be kept, and therefore the assisting effect can be stable.

Preferably the stiffness control unit is configured to change the stiffness of the variable stiffness mechanism transiently. With this configuration, stiffness is changed transiently, which enables assisting of natural walking.

Preferably the stiffness control unit is configured to increase the stiffness of the variable stiffness mechanism if the relative position of the foot end is determined as forward of the reference part, and to decrease the stiffness of the variable stiffness mechanism if the relative position of the foot end is determined as backward of the reference part. With this configuration, the relative position of the foot end is used as additional information in determination, and therefore shift timing can be determined precisely.

Preferably the walking assistance attachment includes a thigh-side link and a lower thigh-side link that are coupled via a rotating member disposed at a position corresponding to a position of the knee, the variable stiffness mechanism includes a driving source attached to one of the thigh-side link and the lower thigh-side link, a supporting member configured to move between a position close to the rotating member and a position away from the rotating member while being driven by the driving source, and an elastic member that extends between the thigh-side link and the lower thigh-side link and passes through the supporting member for detouring between the links, and the stiffness control unit is configured to, as the driving source is controlled for driving, move the supporting member to a position away from the rotating member at shift timing from the swing phase to the stance phase, and move the supporting member to a position close to the rotating member at shift timing from the stance phase to the swing phase. With this configuration, the supporting member can move to the positions close to and away from the rotating member while being driven by the driving source, so that the detouring length can be increased and decreased. Thereby, the expanding amount of the elastic member can be changed, and the stiffness can be changed with a simple configuration.

Preferably, the sensor includes a first attitude sensor attached to the thigh-side link and a second attitude sensor attached to the lower thigh-side link, the first attitude sensor being configured to detect motion in a plane vertical to the thigh-side link, the second attitude sensor being configured to detect motion in a plane vertical to the lower thigh-side link. With this configuration, the attitude sensors are attached to the thigh-side link and the lower-thigh-side link, whereby the relative velocity of the foot end is calculated. This can eliminate a sensor on the sole, and can provide a configuration that is simple, has a long life and enables future prediction.

REFERENCE SIGNS LIST 1 walking assistance attachment
10 upper link (thigh-side link)
11, 21 attitude sensor (sensor)
20 lower link (lower-thigh side link)
30 rotating member
4 variable stiffness mechanism
42 motor (driving source)
43 ball screw
44 nut (supporting member)
441 supporting point
46 linear spring (elastic member)
5 controller
53 foot-end motion calculation part (walking information acquisition unit)
54 leg state determination part(leg state determination unit)
55 motor driving control part (stiffness control unit)

The invention claimed is:

1. A leg-phase shift timing determination apparatus, comprising:
two angle sensors attached to an upper link and a lower link to be fastened correspondingly to a thigh and a lower thigh of a human body;
a walking information acquisition unit configured to successively detect by the two angle sensors motion of the thigh and the lower thigh of the human body as motion of a leg, respectively obtain inclination angles and angular velocities of the thigh and the lower thigh, and successively calculate a relative velocity of a foot end with reference to a reference part of the human body from obtained inclination angles and angular velocities; and
a leg state determination unit configured to determine shift timing between a swing phase and a stance phase based on the relative velocity of the foot end calculated with reference to the reference part of the human body.

2. The leg-phase shift timing determination apparatus according to claim 1, wherein the leg state determination unit is configured to determine shift timing between the swing phase and the stance phase based on the relative velocity of the foot end and positive and negative polarities of the relative velocity.

3. The leg-phase shift timing determination apparatus according to claim 1, wherein the walking information acquisition unit is further configured to successively calculate a relative position of the foot end with reference to a reference part of the human body from the motion of a leg detected by each of the angle sensors; and the leg state determination unit is further configured to, based on whether the relative position of the foot end is positive or negative, determine whether shift timing is from the swing phase to the stance phase or from the stance phase to the swing phase.

4. The leg-phase shift timing determination apparatus according to claim 1, wherein the relative velocity Vx of the foot end is calculated by the following expression:

$$Vx = L1 \cdot \cos(q1) \cdot Vq1 - L2 \cdot \cos(q2) \cdot Vq2,$$

where Vx denotes the relative velocity of the foot end with reference to a waist of the human body, q1 and Vq1 denote an inclination angle and an angular velocity of the thigh, q2 and Vq2 denote an inclination angle and an angular velocity of the lower thigh, and L1 and L2 denote dimensions of the thigh and the lower thigh of the human body.

5. The leg-phase shift timing determination apparatus according to claim 1, wherein the two angle sensors comprise at least one type of an acceleration sensor, a magnetic sensor and a gyro sensor.

6. A walking assistance apparatus, comprising:
a walking assistance attachment to be attached to a leg of a human body and including a variable stiffness mechanism having stiffness that is changeable in a direction where the human bends and stretches the knee;
the leg-phase shift timing determination apparatus according to claim 1; and
a stiffness control unit configured to increase the stiffness of the variable stiffness mechanism at shift timing from the swing phase to the stance phase and to decrease the stiffness of the variable stiffness mechanism at shift timing from the stance phase to the swing phase.

7. The walking assistance apparatus according to claim 6, wherein the stiffness control unit is configured to keep a set current stiffness until starting time of next shift timing.

8. The walking assistance apparatus according to claim 6, wherein the stiffness control unit is configured to change the stiffness of the variable stiffness mechanism transiently.

9. The walking assistance apparatus according to claim 6, wherein the stiffness control unit is configured to increase the stiffness of the variable stiffness mechanism if the relative position of the foot end is determined as forward of the reference part, and to decrease the stiffness of the variable stiffness mechanism if the relative position of the foot end is determined as backward of the reference part.

10. The walking assistance apparatus according to claim 6, wherein the walking assistance attachment includes a thigh-side link and a lower thigh-side link that are coupled via a rotating member disposed at a position corresponding to a position of the knee, the variable stiffness mechanism includes a driving source attached to one of the thigh-side link and the lower thigh-side link, a supporting member configured to move between a position close to the rotating member and a position away from the rotating member while being driven by the driving source, and an elastic member that extends between the thigh-side link and the lower thigh-side link and passes through the supporting member for detouring between the links, and the stiffness control unit is configured to, as the driving source is controlled for driving, move the supporting member to a position away from the rotating member at shift timing from the swing phase to the stance phase, and move the supporting member to a position close to the rotating member at shift timing from the stance phase to the swing phase.

11. The walking assistance apparatus according to claim 10, wherein the two angle sensors include a first angle sensor attached to the thigh-side link and a second angle sensor attached to the lower thigh-side link, the first angle sensor being configured to detect motion in a plane vertical to the thigh-side link, the second angle sensor being configured to detect motion in a plane vertical to the lower thigh-side link.

12. The leg-phase shift timing determination apparatus according to claim 1, wherein said shift timing between said swing phase and said stance phase is determined based on said relative foot end velocity with reference to said reference part of the human body without use of a sensor on the foot of the human body.

13. The leg-phase shift timing determination apparatus according to claim 1, comprising a plurality of sensors including a first angle sensor of said two angle sensors and a second angle sensor of said two angle sensors, said first angle sensor being attached to the upper link corresponding to a thigh region of the human body and said second angle sensor being attached to the lower link corresponding to a lower leg region of the human body, and wherein none among said plurality of sensors is located on a foot of the human body; and wherein all sensor input used to determine said shift timing between said swing phase and said stance phase is obtained only from said plurality of sensors.

14. A method for determining leg-phase shift timing, comprising:

a walking information acquisition step of successively detecting motion of a thigh and a lower thigh of a human body as motion of a leg, by using two angle sensors attached to an upper link and a lower link to be fastened corresponding to the thigh and the lower thigh of the human body, respectively obtaining inclination angles and angular velocities of the thigh and the lower thigh, and successively calculating a relative velocity of a foot end with reference to a reference part of the human body from obtained inclination angles and angular velocities; and a leg state determination step of determining shift timing between a swing phase and a stance phase based on the relative velocity of the foot end with reference to the reference part of the human body calculated at the walking information acquisition step.

15. The method for determining leg-phase shift timing according to claim 14, wherein the leg state determination step includes determining shift timing between the swing phase and the stance phase based on the relative velocity of the foot end and positive and negative polarities of the relative velocity.

16. The method for determining leg-phase shift timing according to claim 14, wherein the walking information acquisition step further includes successively calculating a relative position of a foot end with reference to a reference part of the human body from the motion of a leg detected by each of the angle sensors; and the leg state determination step includes, based on whether the relative position of the foot end is positive or negative, determining whether shift timing is from the swing phase to the stance phase or from the stance phase to the swing phase.

17. The method for determining leg-phase shift timing according to claim 14, wherein said determining said shift timing between said swing phase and said stance phase is based on said relative foot end velocity with reference to said reference part of the human body without use of a sensor on the foot of the human body.

18. A method for controlling walking assistance for a walking assistance attachment to be attached to a leg of a human body and including a variable stiffness mechanism having stiffness that is changeable in a direction where the human bends and stretches the knee, the method comprising;

- a walking information acquisition step of successively detecting motion of a thigh and a lower thigh of a human body as motion of a leg, by using two angle sensors attached to an upper link and a lower link to be fastened corresponding to the thigh and the lower thigh of the human body, respectively obtaining inclination angles and angular velocities of the thigh and the lower thigh, and successively calculating a relative velocity of a foot end with reference to a reference part of the human body from obtained inclination angles and angular velocities;
- a leg state determination step of determining shift timing between a swing phase and a stance phase based on the relative velocity of the foot end with reference to the reference part of the human body calculated at the walking information acquisition step; and
- a stiffness control step of increasing the stiffness of the variable stiffness mechanism at shift timing from the swing phase to the stance phase and decreasing the stiffness of the variable stiffness mechanism at shift timing from the stance phase to the swing phase.

19. The method for determining leg-phase shift timing according to claim 18, wherein said determining said shift timing between said swing phase and said stance phase is based on said relative foot end velocity with reference to said reference part of the human body without use of a sensor on the foot of the human body.

* * * * *